| United States Patent [19] | [11] | 4,277,636 |
|---|---|---|
| Norton et al. | [45] | Jul. 7, 1981 |

[54] PROCESS FOR PREPARING HIGH DENSITY FUELS

[75] Inventors: Richard V. Norton, Dublin; Peter J. Frank; Dennis H. Fisher, both of Westerville; Steven C. Howe, Columbus, all of Ohio

[73] Assignee: Ashland Oil, Inc., Ashland, Ky.

[21] Appl. No.: 176,728

[22] Filed: Aug. 11, 1980

[51] Int. Cl.$^3$ .............................................. C10L 1/04
[52] U.S. Cl. ........................................ 585/14; 585/22; 585/253; 585/362; 149/109.4; 149/109.6; 149/120
[58] Field of Search ................... 585/14, 22, 253, 362; 149/109.4, 109.6, 120

[56] References Cited

U.S. PATENT DOCUMENTS

| 3,381,046 | 4/1968 | Cohen et al. | 585/362 |
|---|---|---|---|
| 4,059,644 | 11/1977 | Cannell | 585/14 |
| 4,086,284 | 4/1978 | Schneider et al. | 585/14 |
| 4,177,217 | 12/1979 | Janoshi et al. | 585/14 |

*Primary Examiner*—Patrick Garvin
*Assistant Examiner*—J. V. Howard
*Attorney, Agent, or Firm*—William Kammerer

[57] ABSTRACT

Method for effecting the formation of co-trimers of cyclopentadiene and methylcyclopentadiene whereby a mixture of the dimers of said dienes is heated in the presence of an inert solvent. The foregoing method is implemented to provide a high energy fuel by substantially completely hydrogenating the resultant trimerization product.

6 Claims, No Drawings

PROCESS FOR PREPARING HIGH DENSITY FUELS

BACKGROUND OF THE INVENTION

1. Field of the Invention

This invention relates to a method for conjointly trimerizing cyclopentadiene and methylcyclopentadiene and the utilization of the resultant trimerization product to prepare a high energy fuel.

2. Description of the Prior Art

High energy hydrocarbon fuels are characterized in having a net volumetric heat of combustion in excess of about 140,000 BTU per gallon. A high energy fuel is essentially required for fueling turbojet and ramjet propelled, limited volume missile systems. Beyond the need for a high energy content in order to maximize range performance of the missile, there are other requirements in the forefront depending, in the main, on the manner in which the missile is to be deployed. For instance, in one type of deployment the fuel must exhibit a very low freezing point and low viscosity combined with high volatility characteristics. In another type, relatively low volatility is critical and a higher freezing point and viscosity acceptable.

A high energy hydrocarbon fuel does not occur in nature but rather must be synthesized which generally involves one or more difficult steps. Essentially all of the current generation of such fuels commonly feature a norbornane moiety having an additional cyclic hydrocarbon appendage. The latter includes the norbornane structure itself in the case of the most exotic of these fuels derived from dihydro di (norbornadiene). In some instances only a certain stereo isomer of the synthesized compound represents a suitable fuel from the standpoint of having the requisite physical properties.

Recently, the hydrogenated Diels-Alder trimer of cyclopentadiene and methylcyclopentadiene has been proposed as an acceptable high energy fuel for use in missile systems of the above-mentioned type. A method for preparing such trimers is set forth in U.S. Pat. No. 4,059,644. This prior art method initially involves the partial in situ dissociation of a mixture of the dimers of cyclopentadiene and methylcyclopentadiene to their respective monomers which then in turn randomly adduct with dimers present in reaction mixture to provide a trimerization product. The resultant reaction mixture is hydrogenated directly or alternatively, the trimers are recovered therefrom and hydrogenated to provide the high energy fuel. The shortcoming of this prior art method is that 40-50% of the converted product consists of tetramers and higher oligomers that are unsuitable for use as a missile fuel. It is accordingly the object of this invention to modify the aforesaid prior art method in order to reduce substantially the formation of tetramers and higher oligomers.

SUMMARY OF THE INVENTION

In the broadest aspect of this invention a method is provided for effecting the co-trimerization of cyclopentadiene and methylcyclopentadiene to yield an oligomeric product whereby the formation of tetramers and higher oligomers is minimized. In accordance with this method a mixture of cyclopentadiene dimer and methylcyclopentadiene dimer is heated in the presence of an inert hydrocarbon solvent to the substantial extinction of the starting dicyclopentadiene reactant. In a further aspect of the invention, the resultant mixture is substantially completely hydrogenated to yield by way of distillation a fraction comprising said trimers having a gross volumetric heating value of at least about 150,000 BTU per gallon.

DESCRIPTION OF THE PREFERRED EMBODIMENTS

In the practice of the present invention the starting materials, viz., cyclopentadiene dimer and methylcyclopentadiene dimer, can be combined in a molar ratio of from 3:1 to 1:3, respectively, and more preferably from 1.1:1 to 1:1.5 on the same basis. Although the prior art teaches that a portion of the indicated reactants can be employed in their monomeric form, this alternative is not desirable from a practical standpoint. This is so because at the contemplated reaction temperature the dimers of both cyclopentadiene and methylcyclopentadiene appear to dissociate at about the rate the timerization reaction takes place. Consequently, there is no particular advantage to such a method of operation which outweighs the necessity for cracking the corresponding dimer as a preliminary step.

Applicable temperatures for carrying out the timerization reaction broadly range from 150°–250° C. A preferred temperature is in the order of 200°–220° C. When employing the respective dimers in the preferred molar ratio range noted above, the reaction is maintained until there is a substantially complete extinction of the cyclopentadiene dimer. This can be conveniently monitored by gas chromatography analysis.

In order to suppress the formation of tetramers and higher oligomers in accordance with this invention, the trimerization reaction is carried out in a suitable pressure vessel in the presence of an inert hydrocarbon solvent. All liquid hydrocarbons free of ethylenic unsaturation represent suitable inert solvents in the context of this invention. From a practical standpoint, however, a solvent should be selected having a boiling point which allows for a facile recovery thereof by distillation from the desired trimerization reaction products. The latter consists essentially of a heart-cut trimer fraction and a cyclopentadiene/methylcyclopentadiene co-dimer forecut fraction. A variety of aromatic, cyclic and acyclic low density hydrocarbons devoid of ethylenic unsaturation and having a boiling point not in excess of about 170° C. are useful for this purpose. Benzene, toluene and xylene are particularly representative of the applicable liquid hydrocarbon solvents. In addition to the foregoing low density hydrocarbons, one can advantageously employ in the practice of this invention a preformed high density cyclic hydrocarbon fuel such as JP-10 (exo-tetrahydrocyclopentadiene) or RJ-4 which consists of a mixture of the endo and exo-isomers of tetrahydromethylcyclopentadiene dimers. For esoteric reasons concerned with the design of high density specialty fuel blends, the indicated high density fuels represent the preferred solvents.

The amount of solvent applicable for carrying out the present invention is from about 10 to 50 volumetric percent based on the total charge to the reactor. More preferably the charge to the reactor is from 15 to 30 parts by volume of solvent and correspondingly from 85 to 70 parts of the dimer reactants. As indicated previously the reaction is desirably carried out in a closed pressure vessel and accordingly autogenous pressures apply. Operating in this manner minimizes the presence of oxygen in the reaction mixture and thus serves to prevent oxidation products forming from the contemplated reactants. Oxidation inhibitors are preferably utilized. A variety of inhibitors such as the substituted phenols are useful for this purpose.

After effecting the trimerization reaction, the completion thereof being noted as described herein above, the product is then hydrogenated. Hydrogenation is carried out at a temperature of from about 80°–160° C. and more preferably in two stages from 80°–120° C. for one/half the hydrogen uptake, then from 150°–180° C. until the uptake of hydrogen is complete. Applicable pressures are from about 10 to 60 atmospheres and more preferably from 15 to 35 atmospheres. A variety of catalysts can be used for this purpose although commercial nickel hydrogenation catalysts are preferred.

Following hydrogenation the reaction product is distilled to remove the solvent employed during the reaction. As mentioned previously, however, it may be desirable to proceed to recover the solvent fraction, a forecut and a heartcut as one complete fraction in the case of using a high density fuel as the solvent. The indicated forecut is a mixture of cyclopentadienemethylcyclopentadiene co-dimers which in itself represents a high density fuel. On the other hand if one desires to obtain separate fractions of the trimerization product as the heartcut, the forecut or co-dimers as well as the solvent employed, this can be readily achieved.

The foregoing recovery schemes are essentially optional practices. The gist of the present invention is that of minimizing the formation of tetramers and higher oligomers as compared to the prior art thereby resulting in a moderately larger trimer fraction and a substantially larger forecut or co-dimers fraction.

EXAMPLE I.

In this example, dicyclopentadiene and methylcyclopentadiene dimers are co-reacted in accordance with the teachings of U.S. Pat. No. 4,059,644. To a one gallon autoclave were charged 1350 grams of dicyclopentadiene, 1650 grams of methylcyclopentadiene dimer and three grams of BHT (butylated hydroxytoluene). The reactants were held at 210° C. for one hour and then completely hydrogenated at a temperature of 150° C. and a hydrogen pressure of 10 atmospheres in the presence of a standard hydrogenation catalyst. The resultant product was then distilled to provide a forecut and a heartcut. The average composition for two identical runs conducted as described are given in Table 1 set forth in Example II hereinbelow.

EXAMPLE II.

Following the general procedure of Example I, 1237.5 grams of methylcyclopentadiene dimer and 1017.5 grams of dicyclopentadiene were reacted in the presence of 750 grams of toluene and three grams BHT. The reaction was carried out for 1.7 hours at a temperature between 190° and 200° C. The resultant product was hydrogenated and distilled under the same conditions employed in Example I to provide a forecut and a heartcut. The results are noted in Table 1 which follows.

TABLE 1

| Reaction Product | Forecut (Co-Dimers) | Heartcut (Co-Trimers) | Polymer Bottoms |
|---|---|---|---|
| Example I | 22.8 | 36.0 | 41.1 |
| Example II | 37.2 | 39.5 | 22.7 |

EXAMPLE III.

This example illustrates the use of a high density fuel as a solvent in accordance with this invention in effecting the co-trimerization of dicyclopentadiene and methylcyclopentadiene dimer. A 0.5 mole charge of each of the indicated dimers along with 28 pounds of exo-tetrahydrodicyclopentadiene (exo-THDC) and 0.4 pounds of BHT were charged to a 30 gallon high pressure reactor. The mixture was heated to 210°–212° C. and held for 75 minutes. The reactor was cooled to 38° C. and 1.5 pounds of G-49B hydrogenation catalyst and 0.5 pounds of charcoal were added to the reaction mixture and conventional hydrogenation commenced at 14 atmospheres pressure and 150° C. Flash distillation of 165 pounds of the crude hydrogenation product after the filtration through a Celite bed to remove the catalyst and charcoal yielded a forecut, heartcut and polymer residue as follows:

Distillation Product:

| Forecut (exo-THDC, RJ-4, co-dimers and co-trimers | 84.5 pounds |
|---|---|
| Heartcut (co-trimers) | 54.9 pounds |
| Polymeric Bottoms | 25.4 pounts |

Fractionating the forecut to remove the exo-THDC component (26.3 pounds) and separating the co-dimers and RJ-4 from the co-trimer provides the following normalized distribution:

| 1. | RJ-4/co-dimers | 46.7 pounds (33.7%) |
|---|---|---|
| 2. | Co-trimers | 66.4 pounds (47.9%) |
| 3. | Polymer | 25.4 pounds (18.4%) |

A typical hydrogenated fuel mixture of methylcyclopentadiene and cyclopentadiene co-trimers has a boiling range of 280°–320° C., a freezing point below −65° F., a flash point >200° F., a pour point −20° to −30° F., and a viscosity of 5921 cps at −25° F. and 72 cps at 0° F. The high density of the liquid (d=1.018±0.02) gives a fuel having a typical net heat content of 152,300 BTU per gallon.

What is claimed is:

1. In a method for the preparation of a trimerization product of cyclopentadiene and methylcyclopentadiene wherein a neat mixture of the dimers of said dienes is heated to effect the progressive partial dissociation thereof to the respective monomers and the reoligomerization of the resultant reaction mixture to provide the trimerization product; the improvement of effecting said dissociation and reoligomerization in the presence of an inert hydrocarbon solvent.

2. The improvement in accordance with claim 1 wherein the inert solvent is toluene.

3. The improvement in accordance with claim 1 wherein the inert solvent is JP-10 or RJ-4.

4. A method of preparing a high density fuel in which the trimerization product in accordance with the improvement of claim 1 is substantially completely hydrogenated.

5. The method of preparing a high density fuel in accordance with claim 4 wherein the inert solvent is JP-10 or RJ-4.

6. A high density fuel composition consisting essentially of the hydrogenation product prepared according to the method of claim 4 distillatively freed of the hydrogenated derivatives of unreacted starting cyclopentadiene and methylcyclopentadiene and oligomeric reaction products boiling above about 320°.

* * * * *